(12) United States Patent
Osoegawa et al.

(10) Patent No.: US 11,771,845 B2
(45) Date of Patent: Oct. 3, 2023

(54) MESH NEBULIZER AND REPLACEMENT MEMBER

(71) Applicant: OMRON HEALTHCARE CO., LTD., Muko (JP)

(72) Inventors: Nobuhiko Osoegawa, Kyoto (JP); Hiroyuki Shino, Kyoto (JP); Takaaki Okanishi, Kyoto (JP); Katsumi Matsuda, Kyoto (JP); Takuya Togawa, Kyoto (JP); Junji Kawamoto, Kyoto (JP); Naoki Uchida, Kyoto (JP); Yuka Tanioka, Kyoto (JP)

(73) Assignee: OMRON HEALTHCARE CO., LTD., Kyoto (JP)

( * ) Notice: Subject to any disclaimer, the term of this patent is extended or adjusted under 35 U.S.C. 154(b) by 850 days.

(21) Appl. No.: 16/840,485

(22) Filed: Apr. 6, 2020

(65) Prior Publication Data

US 2020/0246556 A1 Aug. 6, 2020

Related U.S. Application Data

(63) Continuation of application No. PCT/JP2018/031494, filed on Aug. 27, 2018.

(30) Foreign Application Priority Data

Oct. 20, 2017 (JP) ................. 2017-203839

(51) Int. Cl.
*A61M 11/00* (2006.01)
*A61M 15/00* (2006.01)

(52) U.S. Cl.
CPC ...... *A61M 11/005* (2013.01); *A61M 15/0026* (2014.02); *A61M 15/0085* (2013.01)

(58) Field of Classification Search
CPC ............ A61M 11/005; A61M 15/0026; A61M 15/0001; A61M 15/001; A61M 15/0025;
(Continued)

(56) References Cited

U.S. PATENT DOCUMENTS

2012/0279533 A1* 11/2012 Kato ................. B08B 3/102
134/184
2012/0285446 A1 11/2012 Van Der Mark
(Continued)

FOREIGN PATENT DOCUMENTS

JP 2013-066847 A 4/2013
JP 2013-516266 A 5/2013
(Continued)

OTHER PUBLICATIONS

Official Communication issued in International Patent Application No. PCT/JP2018/031494, dated Oct. 2, 2018.

*Primary Examiner* — Joseph D. Boecker
*Assistant Examiner* — Brian T Khong
(74) *Attorney, Agent, or Firm* — KEATING AND BENNETT, LLP

(57) ABSTRACT

A mesh nebulizer includes a main body with a recessed portion opening upward. The nebulizer includes a cap that covers an upper portion of the main body and a replacement element separate from the main body and the cap and detachably mountable in the recessed portion of the main body while being separated from the cap prior to operation of the nebulizer. The replacement element includes a sheet including a mesh portion, a bottom plate portion, and a sidewall portion. When the cap is closed with respect to the main body, the cap presses the upper edge of the sidewall portion of the replacement element toward an edge portion
(Continued)

around the recessed portion to position the replacement element with respect to a longitudinal axis direction of the main body.

18 Claims, 10 Drawing Sheets

(58) Field of Classification Search
    CPC ............... A61M 15/0085; B05B 17/06; B05B 17/0607; B05B 17/0615; B05B 17/0623
    See application file for complete search history.

(56) References Cited

U.S. PATENT DOCUMENTS

| | | | |
|---|---|---|---|
| 2014/0231538 A1* | 8/2014 | Tabata | ................ B05B 17/0638 239/102.1 |
| 2019/0054258 A1* | 2/2019 | Koike | .................... B05B 17/06 |

FOREIGN PATENT DOCUMENTS

| | | | | |
|---|---|---|---|---|
| JP | 2014-004208 A | 1/2014 | | |
| JP | 2017-202026 A | 11/2017 | | |
| WO | WO-2011083379 A1 * | 7/2011 | ............ | A61M 11/00 |

\* cited by examiner

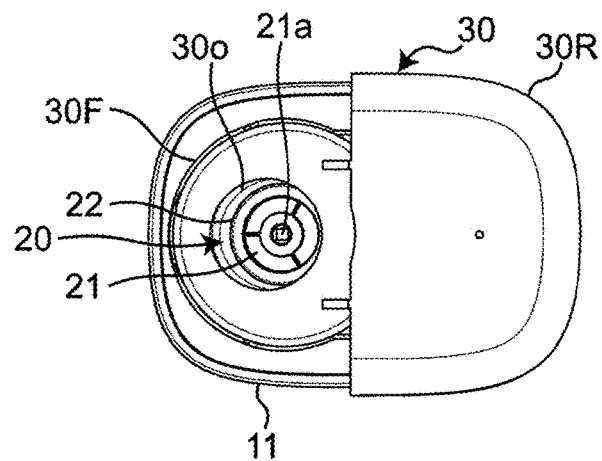
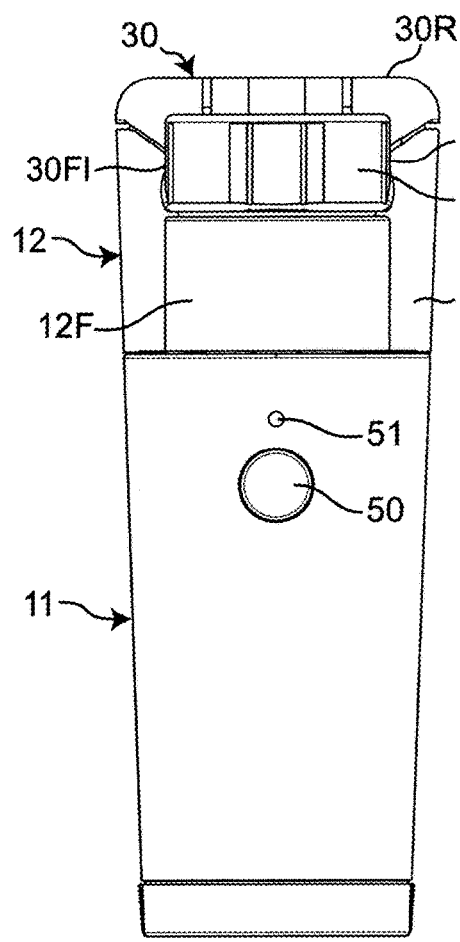
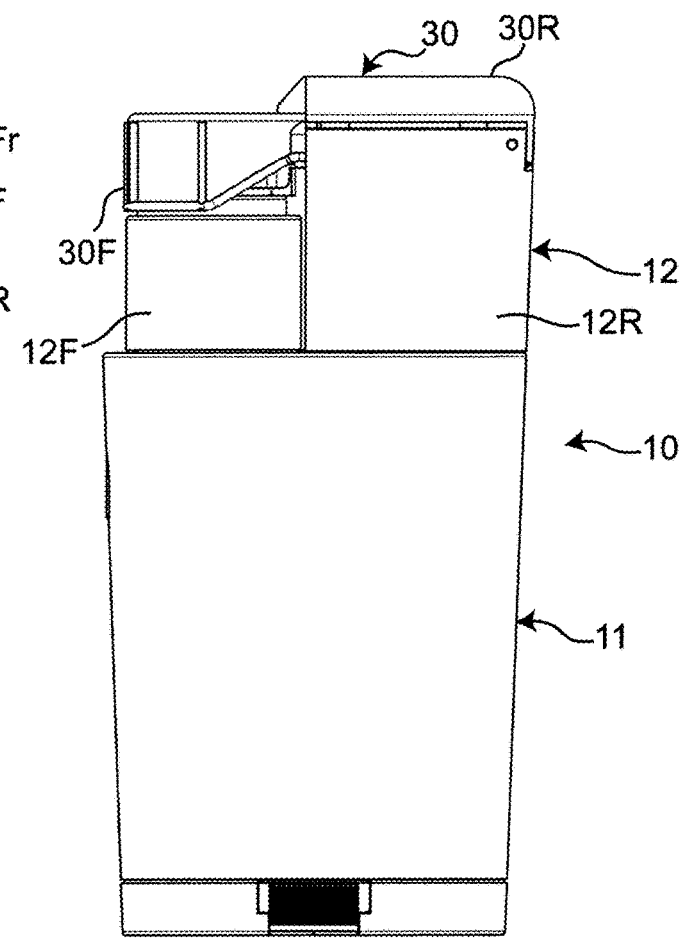

*Fig.8B*
*Fig.8A*
*Fig.8C*
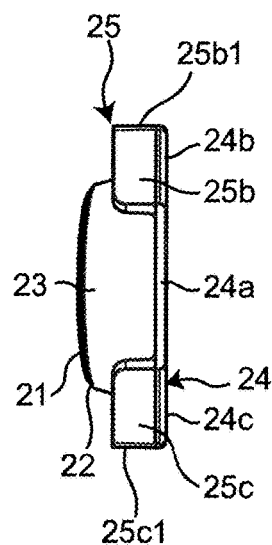
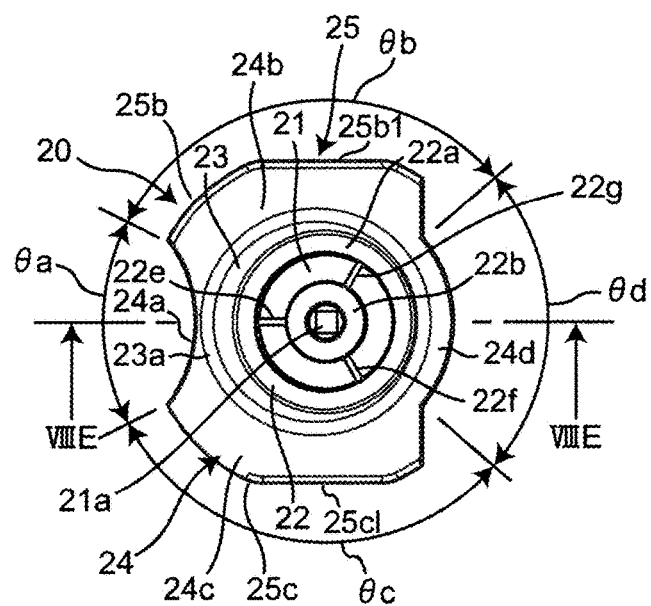
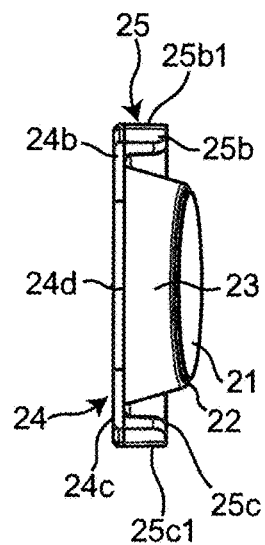
*Fig.8D*
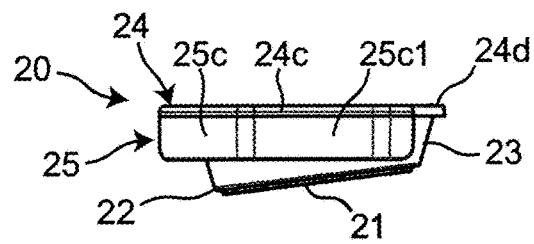

MESH NEBULIZER AND REPLACEMENT MEMBER

CROSS REFERENCE TO RELATED APPLICATIONS

This application claims the benefit of priority to Japanese Patent Application No. 2017-203839 filed on Oct. 20, 2017 and is a Continuation Application of PCT Application No. PCT/JP2018/031494 filed on Aug. 27, 2018. The entire contents of each application are hereby incorporated herein by reference.

BACKGROUND OF THE INVENTION

1. Field of the Invention

The present invention relates to a mesh nebulizer, and more particularly, to a mesh nebulizer to atomize and spray liquid supplied between a vibration surface and a mesh portion through the mesh portion.

The present invention also relates to a replacement element included in a mesh nebulizer.

2. Description of the Related Art

Conventionally, as a mesh nebulizer of this type, for example, as disclosed in JP 2014-4208 A, there is known a mesh nebulizer including a horn transducer in the main body and a mesh cap detachably and openably (pivotably) attached to the main body. In the main body with the mesh cap attached and closed, the vibration surface of the horn transducer faces the mesh portion of the mesh cap. In this state, a medicinal solution is supplied between the vibration surface and the mesh portion, and a drive voltage is applied to the horn transducer to vibrate the vibration surface. This atomizes and sprays the medicinal solution through the mesh portion.

However, in the above mesh nebulizer, it is necessary to remove the mesh cap from the main body and clean, disinfect, and dry the mesh cap including the mesh portion each time after use. Accordingly, it is cumbersome for the user to perform maintenance. Further, because the mesh cap including the mesh portion is a consumable portion, it is necessary to replace the mesh cap in about one year, even if the user performs proper maintenance. Because the mesh cap is relatively large and expensive, there is a problem that the user has to pay a large cost for a replacement element. In addition, if the mesh cap is not properly cleaned, the spray efficiency decreases and the mesh cap becomes unsanitary. Further, because the mesh cap is a precision component, cleaning is difficult.

SUMMARY OF THE INVENTION

Preferred embodiments of the present invention provide mesh nebulizers that are each easy to maintain and significantly reduces a cost for replacement elements.

Other preferred embodiments of the present invention provide replacement elements each included in a mesh nebulizer.

A replacement element according to a preferred embodiment of the present invention is a replacement element of a mesh nebulizer, the mesh nebulizer including a main body and a cap that covers an upper portion of the main body. The main body of the mesh nebulizer includes a recessed portion that opens upward, a vibrator including a vibration surface at a position corresponding to a bottom surface of the recessed portion, and a liquid supplier to supply liquid toward the vibration surface of the vibrator. The replacement element includes a sheet including a mesh portion that faces the vibration surface, a bottom plate portion supporting a peripheral edge of the sheet, and a sidewall portion that is continuous with an outer edge of the bottom plate portion and faces a side surface of the recessed portion. The bottom plate portion of the replacement element includes a flat annular peripheral edge portion supporting an upper surface of the peripheral edge of the sheet and having an inner diameter larger than a diameter of the vibration surface, a flat ring portion that is concentric with the peripheral edge portion, has an outer diameter smaller than the inner diameter of the peripheral edge portion, and supports a corresponding portion of the sheet, and a plurality of elongated ribs radially connecting the peripheral edge portion and the ring portion to each other. The replacement element is separate from the main body and the cap, and is detachably mountable in the recessed portion of the main body while being separated from the cap prior to operation of the mesh nebulizer. When the replacement element is detachably mounted in the recessed portion of the main body while being separated from the cap prior to operation of the mesh nebulizer and the cap is closed with respect to the main body, the replacement element is positioned with respect to a longitudinal axis direction of the main body as the cap presses an upper edge of the sidewall portion toward an edge portion around the recessed portion of the main body.

The "mesh portion" refers to an element that includes a plurality of through holes extending through a sheet and that atomizes liquid by passing the solution through the through holes.

The planar shape of the recessed portion of the main body widely includes an annular shape, for example, a circular or substantially circular shape, a round corner rectangular shape (a rectangular or substantially rectangular shape with rounded corners) or the like. The planar shape of the sidewall portion of the replacement element is the same as or similar to the planar shape of the recessed portion.

The "longitudinal axis direction" of the main body generally refers to a vertical or substantially vertical direction.

A mesh nebulizer according to another preferred embodiment of the present invention is a mesh nebulizer to atomize and spray liquid through a mesh portion. The mesh nebulizer includes a main body including a recessed portion opening upward, a vibrator including a vibration surface at a position corresponding to a bottom surface of the recessed portion, and a liquid supplier to supply liquid toward the vibration surface of the vibrator. The mesh nebulizer further includes a cap that covers an upper portion of the main body and a replacement element that is separate from the main body and the cap and is detachably mountable in the recessed portion of the main body while being separated from the cap prior to operation of the nebulizer. The replacement element includes a sheet including a mesh portion that faces the vibration surface, a bottom plate portion supporting a peripheral edge of the sheet, and a sidewall portion that is continuous with an outer edge of the bottom plate portion and faces a side surface of the recessed portion. The bottom plate portion includes a flat annular peripheral edge portion supporting an upper surface of the peripheral edge of the sheet and having an inner diameter larger than a diameter of the vibration surface, a flat ring portion that is concentric with the peripheral edge portion, has an outer diameter smaller than the inner diameter of the peripheral edge portion, and supports a corresponding portion of the sheet, and a plurality of elongated ribs radially connecting the peripheral edge portion and the ring portion to each other. When the replacement element is detachably mounted in the recessed portion of the main body while being separated from the cap prior to operation of the nebulizer and the cap is closed with respect to the main body, the replacement element is positioned with respect to a longitudinal axis direction of the main body as the cap presses an upper edge of the sidewall portion of the replacement element toward an edge portion around the recessed portion of the main body.

The above and other elements, features, steps, characteristics and advantages of the present invention will become more apparent from the following detailed description of the preferred embodiments with reference to the attached drawings.

BRIEF DESCRIPTION OF THE DRAWINGS

FIG. 5A is a view showing a state in which the mesh nebulizer is assembled (assembled state) as viewed from the right side. FIGS. 5B and 5C are views showing the mesh nebulizer in FIG. 5A as viewed from the front and the top, respectively.

FIG. 8A is a plan view showing the replacement element. FIGS. 8B to 8D are views showing the replacement element as viewed from the left, right, and bottom in FIG. 8A, respectively.

DETAILED DESCRIPTION OF THE PREFERRED EMBODIMENTS

The present invention will become more fully understood from the detailed description given hereinbelow and the accompanying drawings which are given by way of illustration only, and thus are not limitative of the present invention. Preferred embodiments of the present invention will be described in detail below with reference to the drawings.

Figure 1:
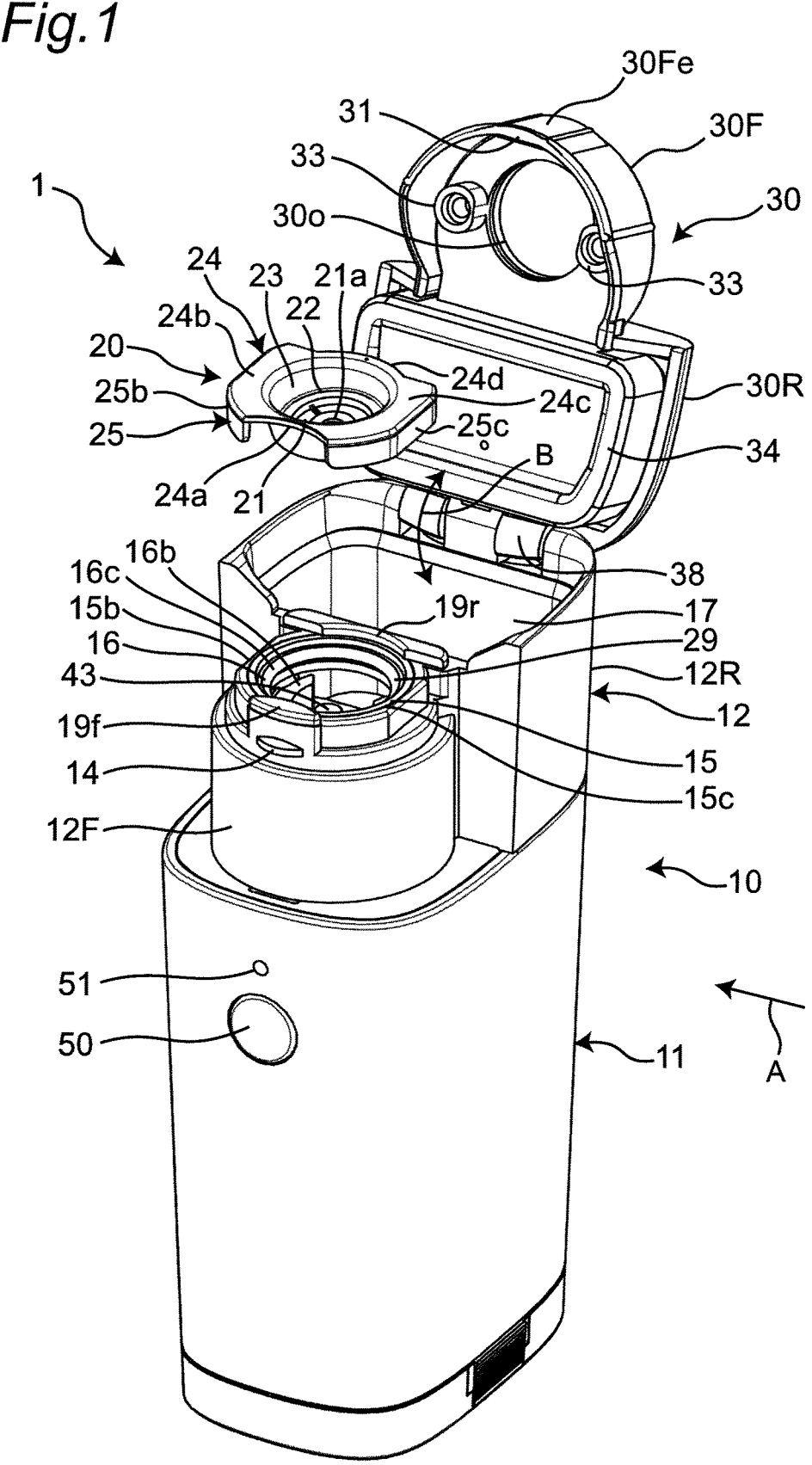
FIG. 1 is a perspective view showing a mesh nebulizer according to a preferred embodiment of the present invention in an exploded state.
Figure 2:
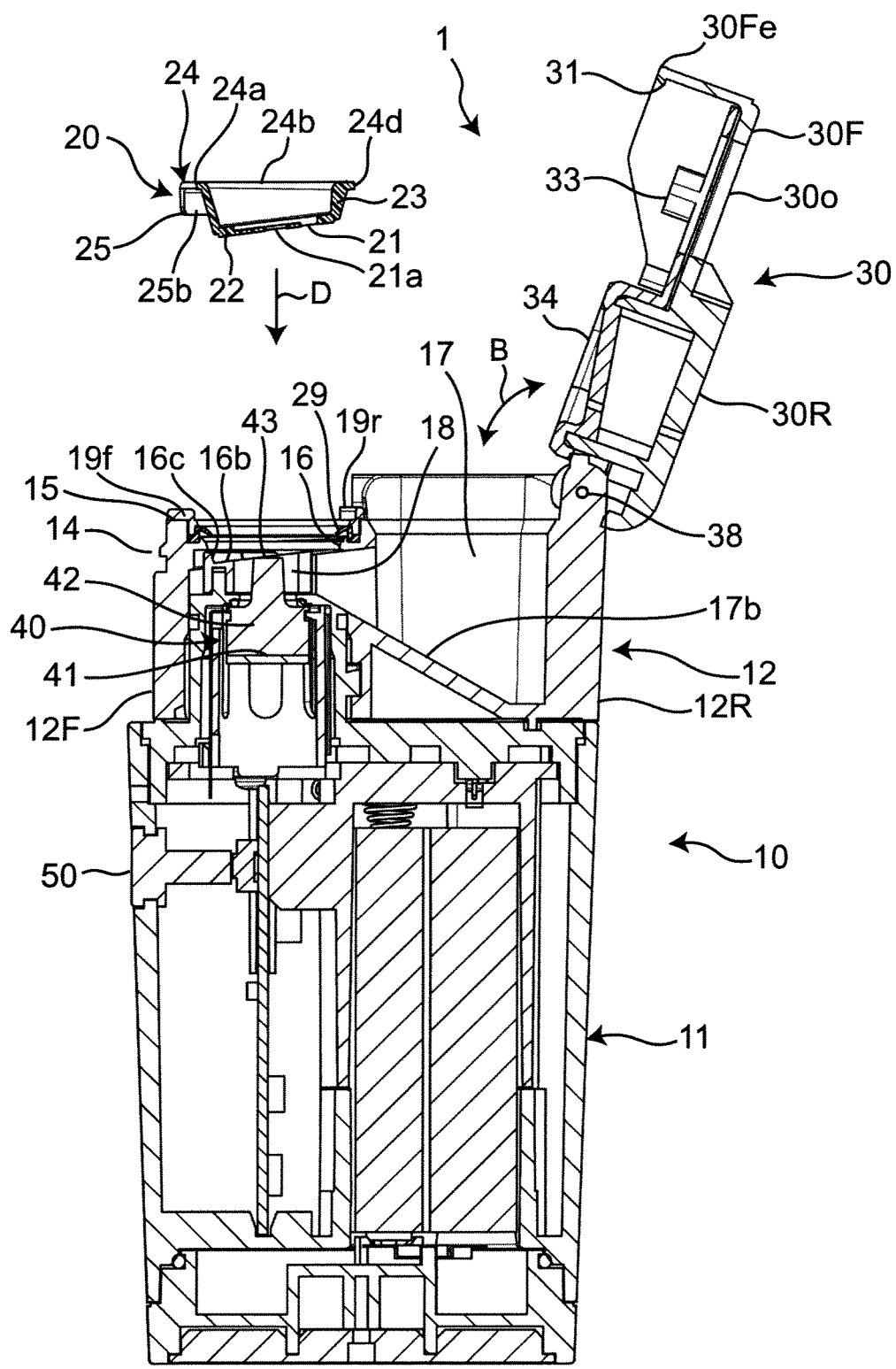
FIG. 2 is a view showing a longitudinal section when the mesh nebulizer in the exploded state in FIG. 1 is viewed from the right side.

FIG. 1 shows a mesh nebulizer 1 according to a preferred embodiment of the present invention as viewed obliquely in an exploded state. FIG. 2 shows a longitudinal section when the mesh nebulizer 1 in the exploded state in FIG. 1 is viewed from the right side (the direction indicated by an arrow A in FIG. 1).

As shown in FIGS. 1 and 2, the mesh nebulizer 1 includes a main body lower portion 11 having a substantially elliptic cylindrical outer shape and a main body upper portion 12 detachably fitted to the main body lower portion 11 from above. A front half portion 12F of the main body upper portion 12 has a substantially columnar outer shape, and a rear half portion 12R of the main body upper portion 12 has a substantially trapezoidal columnar outer shape. The main body lower portion 11 and the main body upper portion 12 define a main body 10.

As shown in FIG. 1, the front surface of the main body lower portion 11 is provided with a power switch 50 to turn on and off the power supply to the nebulizer 1 and an LED lamp 51 to notify operation states of the nebulizer 1. A control system described herein is primarily mounted inside the main body lower portion 11.

The upper surface of the front half portion 12F of the main body upper portion 12 is provided with a recessed portion 16 having a substantially circular planar shape opened upward to receive a replacement element 20 described herein. As clearly shown in FIG. 2, the recessed portion 16 has a bottom surface 16b that is inclined with respect to the longitudinal axis direction (vertical or substantially vertical direction) of the main body 10 and a side surface 16c that continues to the bottom surface 16b and gradually opens upward. Further, as shown in FIG. 1, ridges 19f and 19r are provided at azimuths (the front side and the rear side in this case) on an edge portion 15 around the recessed portion 16. The front ridge 19f has a planar shape protruding in an arc shape toward the center of the recessed portion 16. The rear ridge 19r has a planar shape recessed in an arc shape when viewed from the center of the recessed portion 16. The ridges 19f and 19r are to be fitted to flange portions 24a and 24d of the replacement element 20 (be described herein). Further, as shown in FIG. 2, a packing 29, which is an annular elastic body, is provided on the side surface 16c of the recessed portion 16 of the main body 10 to surround and be in contact with a sidewall portion 23 of the replacement element 20 (described herein) in the circumferential direction.

A vibrator 40 is provided inside the front half portion 12F of the main body upper portion 12 at a position corresponding to the recessed portion 16. The vibrator 40 includes an ultrasonic transducer 41 at a position spaced away and downward from the recessed portion 16, a vibration surface 43 that is horizontal or substantially horizontal at a position corresponding to the bottom surface 16b of the recessed portion 16, and a horn 42 between the ultrasonic transducer 41 and the vibration surface 43 and amplifies and transmits the vibration of the ultrasonic transducer 41 to the vibration surface 43. The drive voltage for the ultrasonic transducer 41 is supplied from the main body lower portion 11 via a contact electrode provided between the main body upper portion 12 and the main body lower portion 11.

Further, as shown in FIG. 1, a liquid storage portion 17 having a substantially semicircular planar shape is provided in the rear half portion 12R of the main body upper portion 12. As shown in FIG. 2, the liquid storage portion 17 has a bottom surface 17b that becomes gradually shallower toward the front side. Further, a liquid supply path 18 to supply a liquid (medicinal solution) from the liquid storage portion 17 onto the vibration surface 43 of the vibrator 40 is continuous with the front side portion of the liquid storage portion 17. The liquid storage portion 17 and a liquid supply path 18 define a liquid supplier. In the exploded state in FIGS. 1 and 2, the liquid storage portion 17 is open upward.

Therefore, the user is able to put a medicinal solution into the liquid storage portion 17 from above.

A cap 30 that defines and functions as a lid is coupled to the upper edge of the rear end side of the rear half portion 12R of the main body upper portion 12, the cap 30 being pivotal through a hinge 38 with respect to the main body upper portion 12 as shown by a bidirectional arrow B. The cap 30 includes a rear half portion 30R having a substantially trapezoidal planar shape and provided on a side adjacent to or in a vicinity of the hinge 38 and a front half portion 30F having an annular and substantially circular planar shape and continuing to the rear half portion 30R. On a side of the front half portion 30F of the cap 30 facing the upper surface of the main body upper portion 12, two cylindrical protruding portions 33, 33 protrude at positions corresponding to a left-side portion 15b and a right-side portion 15c of the edge portion 15 around the recessed portion 16. On a side of the rear half portion 30R of the cap 30 facing the upper surface of the main body upper portion 12, a mesa portion 34 having a substantially trapezoidal planar shape corresponding to the planar shape of the liquid storage portion 17 is provided. As will be described herein, in a state in which the cap 30 is closed with respect to the main body upper portion 12 and the mesh nebulizer 1 is assembled, the protruding portions 33, 33 work to position the replacement element 20. In addition, the mesa portion 34 blocks the upper portion of the liquid storage portion 17 to significantly reduce or prevent overflow of a medicinal solution from the liquid storage portion 17. The center of the front half portion 30F of the cap 30 is an opening 30o to which a mouthpiece or the like is to be attached.

Figure 7:
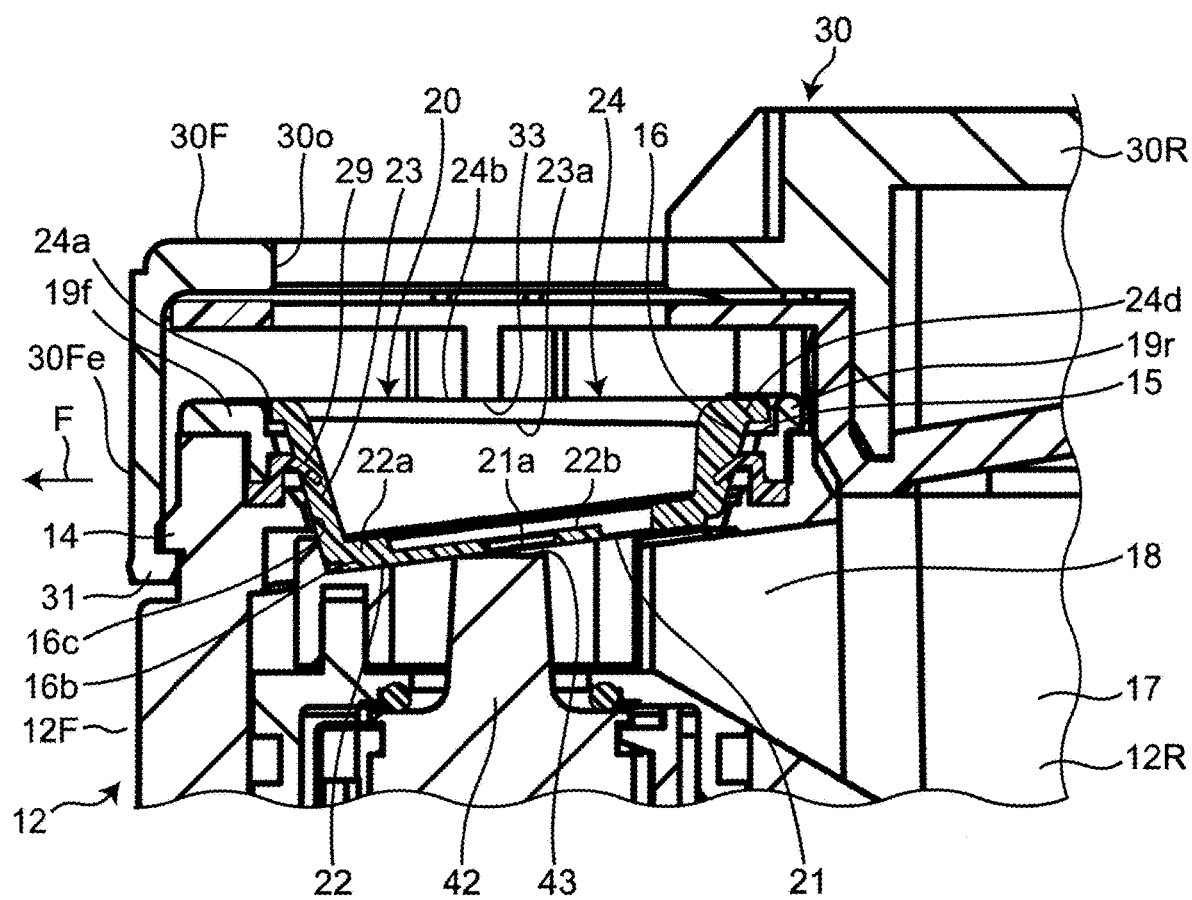
FIG. 7 is an enlarged view showing a portion adjacent to or in a vicinity of a replacement element in FIG. 6.

An engagement protrusion 31 protruding inward is provided on a front edge 30Fe (on the opposite side to the hinge 38) of the front half portion 30F of the cap 30. On the other hand, an engagement protrusion 14 protruding outward (forward) from the front end is provided on the front half portion 12F of the main body upper portion 12. When the cap 30 is closed with respect to the main body upper portion 12, as shown in FIG. 7, the engagement protrusion 31 of the cap 30 is engaged with the engagement protrusion 14 of the main body upper portion 12 in the vertical or substantially vertical direction. That is, once the engagement protrusion 31 of the cap 30 is engaged with the engagement protrusion 14 of the main body upper portion 12, the engagement protrusion 31 comes into contact with the engagement protrusion 14 to significantly reduce or prevent upward movement of the front half portion 30F of the cap 30 from below with respect to the front half portion 12F of the main body upper portion 12. Accordingly, the cap 30 may be fixed to the main body upper portion 12 in a closed state. When opening the cap 30 with respect to the main body, the user holds and presses a left portion 30Fl and a right portion 30Fr (shown in FIG. 5B) of the front half portion 30F of the cap 30 by hand (for example, the thumb and the forefinger). As a result, the front edge 30Fe of the front half portion 30F of the cap 30 is deformed forward (in the direction of an arrow F shown in FIG. 7), and the engagement by the engagement protrusion 31 and the engagement protrusion 14 is released. Accordingly, the user is able to easily fix or release the cap 30 with respect to the main body 10 (the main body upper portion 12). Further, the cap 30 will never be lost.

FIGS. 1 and 2 show the replacement element 20 formed separately from the main body 10 and the cap 30. Prior to operation of the nebulizer 1, the replacement element 20 is detachably mounted in the recessed portion 16 of the main body upper portion 12 in a state in which the replacement element 20 is separated from the cap 30.

Figure 8E:
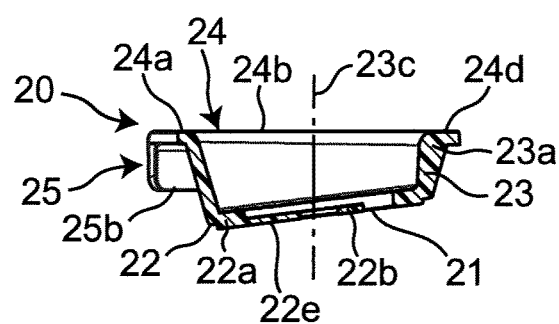
FIG. 8E is a view showing a cross section taken along line VIIIE-VIIIE in FIG. 8A.

FIGS. 8A to 8F show elements and portions of the replacement element 20. As shown in FIGS. 8A and 8E, the replacement element 20 includes a flat film-shaped sheet 21 that faces the vibration surface 43 (see FIGS. 1 and 2), a bottom plate portion 22 that supports the sheet 21, an annular sidewall portion 23 that is continuous with the outer edge of the bottom plate portion 22 and faces the side surface 16c of the recessed portion 16 (see FIGS. 1 and 2), a flange portion 24 that is continuous with an upper edge 23a of the sidewall portion 23 and extends radially outward around the upper edge 23a, and a knob margin portion 25 that is continuous with and extends downward from an outer edge of a portion of the flange portion 24 (flange portions 24b and 24c described herein).

The sheet 21 is bonded or welded to the lower surface of the bottom plate portion 22. A substantially central region of the sheet 21 defines and functions a mesh portion 21a.

The bottom plate portion 22 includes a flat annular peripheral edge portion 22a that supports the upper surface of the peripheral edge of the sheet 21 and has an inner diameter larger than the diameter of the vibration surface 43, a flat ring portion 22b that is concentric with the peripheral edge portion 22a, has an outer diameter smaller than the inner diameter of the peripheral edge portion 22a, and supports the corresponding portion of the sheet 21, and a plurality of (for example, three in this case) elongated ribs 22e, 22f, and 22g that connect the peripheral edge portion 22a and the ring portion 22b to each other in the radial direction and support the corresponding portions of the sheet 21. The ring portion 22b is attached to maintain the mesh portion 21a as flat as possible and adjust the natural frequency of the sheet 21 including the mesh portion 21a. The thicknesses of the ring portion 22b and the ribs 22e, 22f, and 22g are smaller than the thickness of the peripheral edge portion 22a (see FIG. 8E). The lower surfaces of the ring portion 22b and the ribs 22e, 22f, and 22g are flush with the lower surface of the peripheral edge portion 22a to support the sheet 21. The thickness of the peripheral edge portion 22a is about 1 mm, for example. The thicknesses of the ring portion 22b and the ribs 22e, 22f, and 22g are about 400 μm, for example.

Figure 8F:
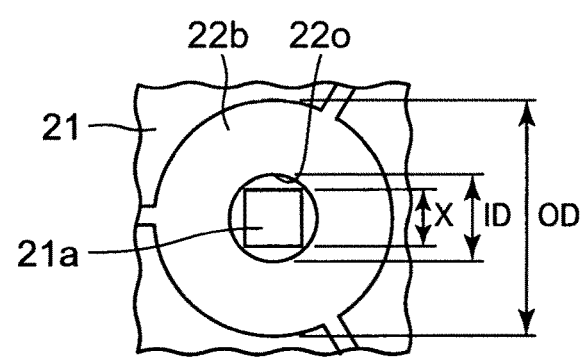
FIG. 8F is an enlarged view showing a portion adjacent to or in a vicinity of the mesh portion in FIG. 8A.

As shown in an enlarged scale in FIG. 8F, the mesh portion 21a is formed by providing many through holes (not shown), each having a diameter of about 3 μm in a square region having side dimension X=about 1.5 mm in the sheet 21 having a thickness of about 30 μm, for example. The inner diameter dimension (ID) and the outside dimension (OD) of the ring portion 22b are respectively ID=about 2.2 mm and OD=about 6.0 mm, for example. The mesh portion 21a is located in a central opening 22o of the ring portion 22b to release atomized medicinal solution via the through holes.

The mesh portion 21a of the sheet 21 is maintained flatter by the ring portion 22b. Therefore, the mesh portion 21a is able to be to more accurately located with respect to the vibration surface 43 in a state in which the replacement element 20 is mounted in the recessed portion 16 of the main body 10, and the spray efficiency is increased.

As shown in FIGS. 8A to 8D, the flange portion 24 is divided into four portions (these portions are referred to as flange portions 24a, 24b, 24c, and 24d) around the center 23c of the annular sidewall portion 23. The flange portions 24b and 24c occupy two angular ranges θb and θc corresponding to opposite azimuths (the upper side and the lower side in FIG. 8A). The flange portions 24a and 24d occupy remaining two angular ranges θa and θd respectively corresponding to azimuths on the left side and the right side in FIG. 8A. The flange portion 24a occupies the angular range θa of about 60° as viewed from the center 23c (shown in FIG. 8E) of the sidewall portion 23. The planar shape of the outer edge of the flange portion 24a (the shape in a plane perpendicular or substantially perpendicular to the center 23c of the sidewall portion 23) is an arc shape recessed inward to fit on the front ridge 19f around the recessed portion 16 of the main body 10. The flange portions 24b and 24c occupy the angular ranges θb and θc, each of about 110°, as viewed from the center 23c of the sidewall portion 23. The planar shapes of the outer edges of the flange portions 24b and 24c are substantially arc-shaped, but portions of the outer edges which correspond to the azimuths directly above and below (azimuths opposite to each other) in FIG. 8A are linear. These flange portions 24b and 24c overlap the left-side portion 15b and the right-side portion 15c of the edge portion 15 around the recessed portion 16 of the main body 10, respectively. The flange portion 24d occupies the angular range θd of about 80° as viewed from the center 23c of the sidewall portion 23. The planar shape of the outer edge of the flange portion 24d is an arc shape bulging outward to fit on the ridge 19r on the rear side around the recessed portion 16 of the main body 10. As a result, the planar shape of the outer edge of the flange portion 24 is different from an original planar shape before rotation when rotated through about 180° around the center 23c of the sidewall portion 23.

The knob margin portion 25 includes a portion (to be referred to as a knob margin portion 25b) continuous with and extending downward from the outer edge of the flange portion 24b and a portion (to be referred to as a knob margin portion 25c) continuous with and extending downward from the outer edge of the flange portion 24c. Of the knob margin portions 25b and 25c, portions 25b1 and 25c1 respectively corresponding to the azimuths directly above and directly below (azimuths opposite to each other) in FIG. 8A are flat in accordance with the linear shapes of the corresponding portions of the outer edges of the flange portions 24b and 24c.

The dimension of each of the flange portions 24b and 24c of the replacement element 20 which extends outward is set to be larger than the dimension of the flange portions 24a and 24d which extends outward. Accordingly, when mounting the replacement element 20 in the recessed portion 16 of the main body 10, the user is able to determine the azimuth around the center 23c of the sidewall portion 23 of the replacement element 20 based on the dimension of the flange portion 24 which extends outward.

As a result, as is clear from FIG. 8A, the planar shape of the outer edge of the flange portion 24 is different from an original planar shape before rotation when rotated through about 180° around the center of the sidewall portion 23. That is, the planar shape of the outer edge of the flange portion 24 does not have two-fold rotational symmetry around the center 23c of the sidewall portion 23. Accordingly, it is possible to prevent the replacement element 20 from being attached (mistakenly) to the main body 10 in a posture rotated through about 180° around the center of the sidewall portion 23 with respect to the proper posture.

The replacement element 20 allows the user to pick the knob margin portions 25b and 25c, together with the outer edges of the flange portions 24b and 24c, with the user's hand (for example, the thumb and the forefinger), from both sides (outside) toward the center. Accordingly, the user is able to easily hold the replacement element 20 without touching the mesh portion 21a with the user's fingers. In particular, of the knob margin portions 25b and 25c, the portions 25b1 and 25c1 respectively corresponding to the azimuths directly above and directly below (azimuths opposite to each other) in FIG. 8A are flat, and hence the user is able to easily hold the replacement element 20.

As is obvious from FIG. 8E, the sheet 21 (including the mesh portion 21a) and the bottom plate portion 22 of the replacement element 20 are inclined with respect to the center 23c of the sidewall portion 23 in accordance with the bottom surface 16b (see FIG. 2) of the recessed portion 16 of the main body 10. Further, the sidewall portion 23 of the replacement element 20 gradually opens upward in correspondence with the side surface 16c (see FIG. 2) of the recessed portion 16 of the main body 10.

The elements and components of the replacement element 20, that is, the sheet 21, the bottom plate portion 22, the sidewall portion 23, the flange portion 24, and the knob margin portion 25, include a synthetic resin (including an adhesive when the sheet 21 is bonded to the bottom plate portion 22 with the adhesive). Therefore, the replacement element 20 is able to be manufactured at low cost. Examples of the synthetic resin forming the replacement element 20 include polyamide-based resins, polyester, syndiopolystyrene, polysulfone, polyethersulfone, polyetheretherketone, polyetherimide, polyamideimide, PPS (polyphenylene sulfide), epoxy, phenol, and polyimide. In particular, the bottom plate portion 22, the sidewall portion 23, the flange portion 24, and the knob margin portion 25 defining the replacement element 20 include a synthetic resin that is homogeneously or substantially homogeneously and continuously integrated. It is therefore possible to manufacture the replacement element 20 inexpensively by integral molding.

Figure 9:
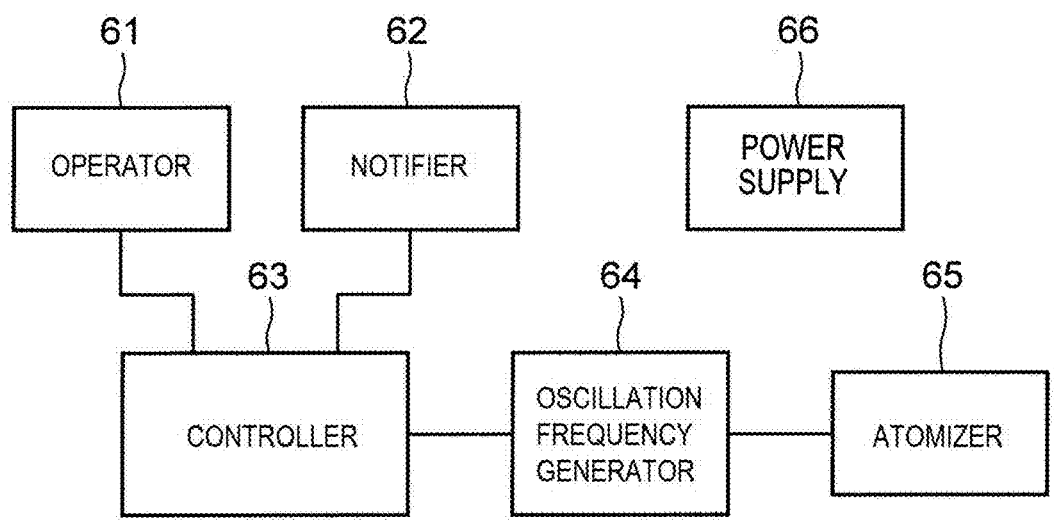
FIG. 9 is a view showing a block diagram of a control system mounted on the main body of the mesh nebulizer.

FIG. 9 shows a block diagram of a control system mounted on the main body 10 of the mesh nebulizer 1. The mesh nebulizer 1 includes an operator 61, a notifier 62, a controller 63, an oscillation frequency generator 64, an atomizer 65, and a power supply 66. The operator 61 includes the power switch 50 shown in FIG. 1. The notifier 62 includes the LED lamp 51 shown in FIG. 1, and may further include a buzzer (not shown). The oscillation frequency generator 64 applies an AC drive voltage to the atomizer 65 based on a control signal from the controller 63. This drive voltage is output, for example, over an output time after the power switch 50 is pressed. The output time may be measured by a timer (not shown). The atomizer 65 includes the vibrator 40 and the mesh portion 21a of the replacement element 20 shown in FIG. 1. An AC drive voltage from the oscillation frequency generator 64 is applied to the ultrasonic transducer 41 of the vibrator 40 of the atomizer 65. The vibration of the ultrasonic transducer 41 is amplified and transmitted to the vibration surface 43 by the horn 42. When the vibration surface 43 vibrates, the medicinal solution supplied to the gap between the vibration surface 43 and the mesh portion 21a is atomized and sprayed through the mesh portion 21a. The controller 63 includes a CPU (Central Processing Unit), sends a signal to the atomizer 65 via the oscillation frequency generator 64, and controls the amount of atomization, the continuous operation time, and the like. In addition, the controller 63 notifies, for example, that the power is turned on by turning on the LED lamp 51 and that the battery capacity is insufficient by blinking the LED lamp 51. The power supply 66 includes a battery (for example, a DC3V chargeable/dischargeable secondary battery), and supplies power to each component or element of the control system.

The user who intends to operate the mesh nebulizer 1 detachably mounts the replacement element 20 including the mesh portion 21a in the recessed portion 16 with a shape opening upward relative to the main body 10 in a state where the cap 30 opens with respect to the main body 10 as shown in FIGS. 1 and 2 and the replacement element 20 is separated from the cap 30 as indicated by an arrow D in FIG. 2.

As described above, at the time of mounting the replacement element 20, the replacement element 20 allows the user to pick the knob margin portions 25*b* and 25*c*, together with the outer edges of the flange portions 24*b* and 24*c*, with the user's hand (for example, the thumb and the forefinger), from both sides (outside) toward the center. Accordingly, the user is able to easily hold the replacement element 20 without touching the mesh portion 21*a* with the user's fingers. Therefore, the user is able to easily mount the replacement element 20 in the recessed portion 16 of the main body 10. In particular, when the user mounts the replacement element 20 while hand portions (for example, the little finger and the palm) other than those pinching the outer edges of the flange portions 24*b* and 24*c* of the replacement element 20 and the knob margin portions 25*b* and 25*c* are in contact with a side surface of the main body 10 or the like, it is possible to easily reduce or prevent the displacement (shake) of the hand with respect to the main body 10. Therefore, the user is further able to easily mount the replacement element 20 in the recessed portion 16 of the main body 10.

When mounting the replacement element 20, as described above, the user is able to determine the azimuth around the center 23*c* of the sidewall portion 23 of the replacement element 20 based on the dimension of the flange portion 24 which extends outward and the planar shape of the outer edge of the flange portion 24. When the user fits the flange portions 24*a* and 24*d* of the replacement element 20 on the ridges 19*f* and 19*r* around the recessed portion 16 of the main body 10, respectively, the replacement element 20 is positioned relative to the recessed portion 16 in the circumferential direction.

As described above, the side surface 16*c* of the recessed portion 16 of the main body 10 gradually opens upward. Further, the sidewall portion 23 of the replacement element 20 gradually opens upward in correspondence with the side surface 16*c* (see FIG. 2) of the recessed portion 16 of the main body 10. Therefore, if the user places the replacement element 20 around the recessed portion 16 when mounting the replacement element 20, the sidewall portion 23 of the replacement element 20 is guided downward by the side surface 16*c* of the recessed portion 16.

The bottom surface 16*b* of the recessed portion 16 of the main body 10 is inclined with respect to the longitudinal axis direction (vertical or substantially vertical direction) of the main body 10, and the mesh portion 21*a* and the bottom plate portion 22 of the replacement element 20 are inclined with respect to the center 23*c* of the sidewall portion 23 in correspondence with the bottom surface 16*b* of the recessed portion 16 of the main body 10. Therefore, if the user places the replacement element 20 around the recessed portion 16 when mounting the replacement element 20, the mesh portion 21*a* and the bottom plate portion 22 of the replacement element 20 are guided in correspondence with the bottom surface 16*b* of the recessed portion 16 of the main body 10. This helps to position the replacement element 20 with respect to the recessed portion 16 in the circumferential direction and the longitudinal axis direction.

Figure 3:
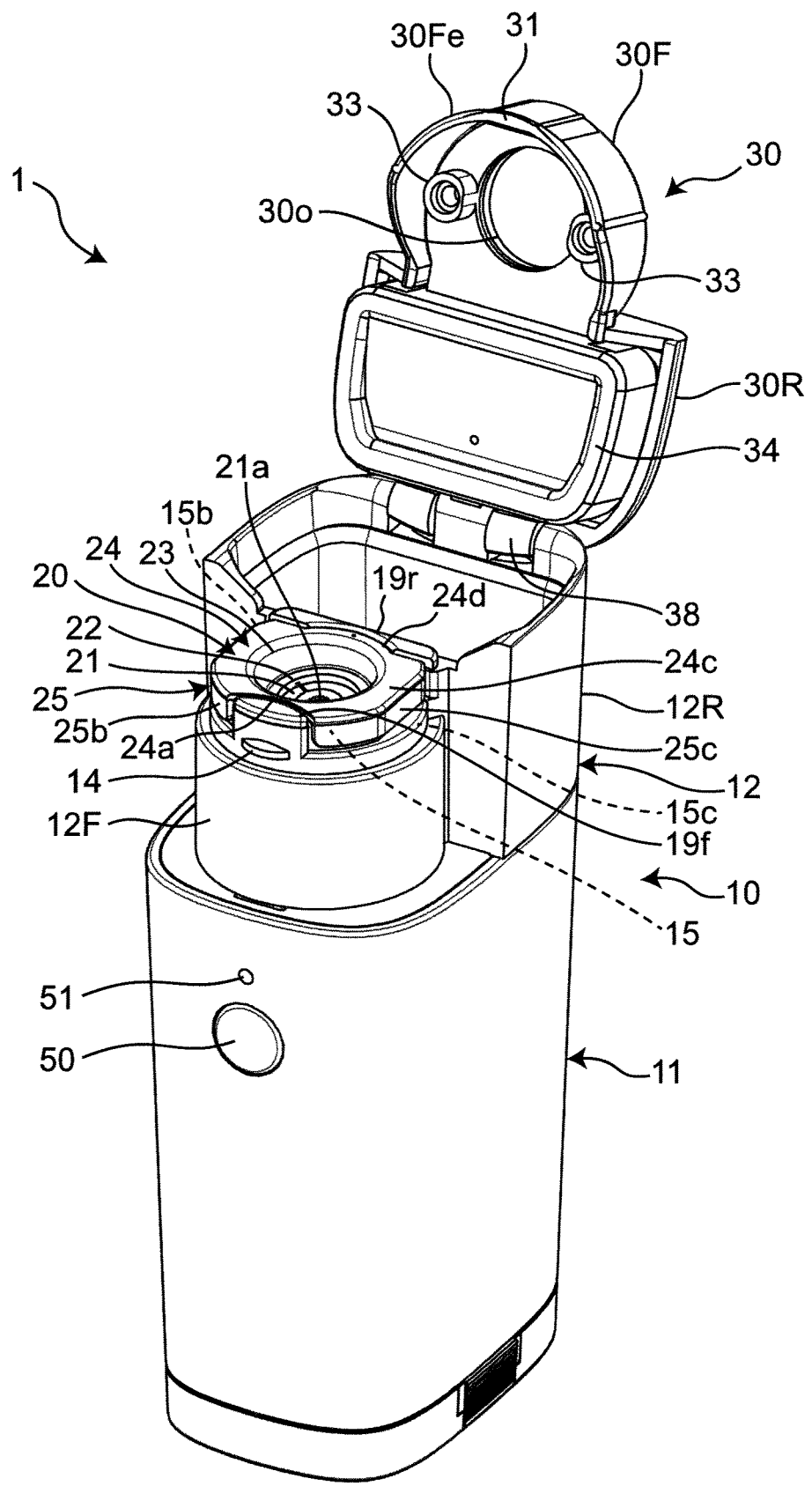
FIG. 3 is a perspective view showing a state in which a replacement element including a mesh portion is mounted on the mesh nebulizer (a mounted state).
Figure 4:
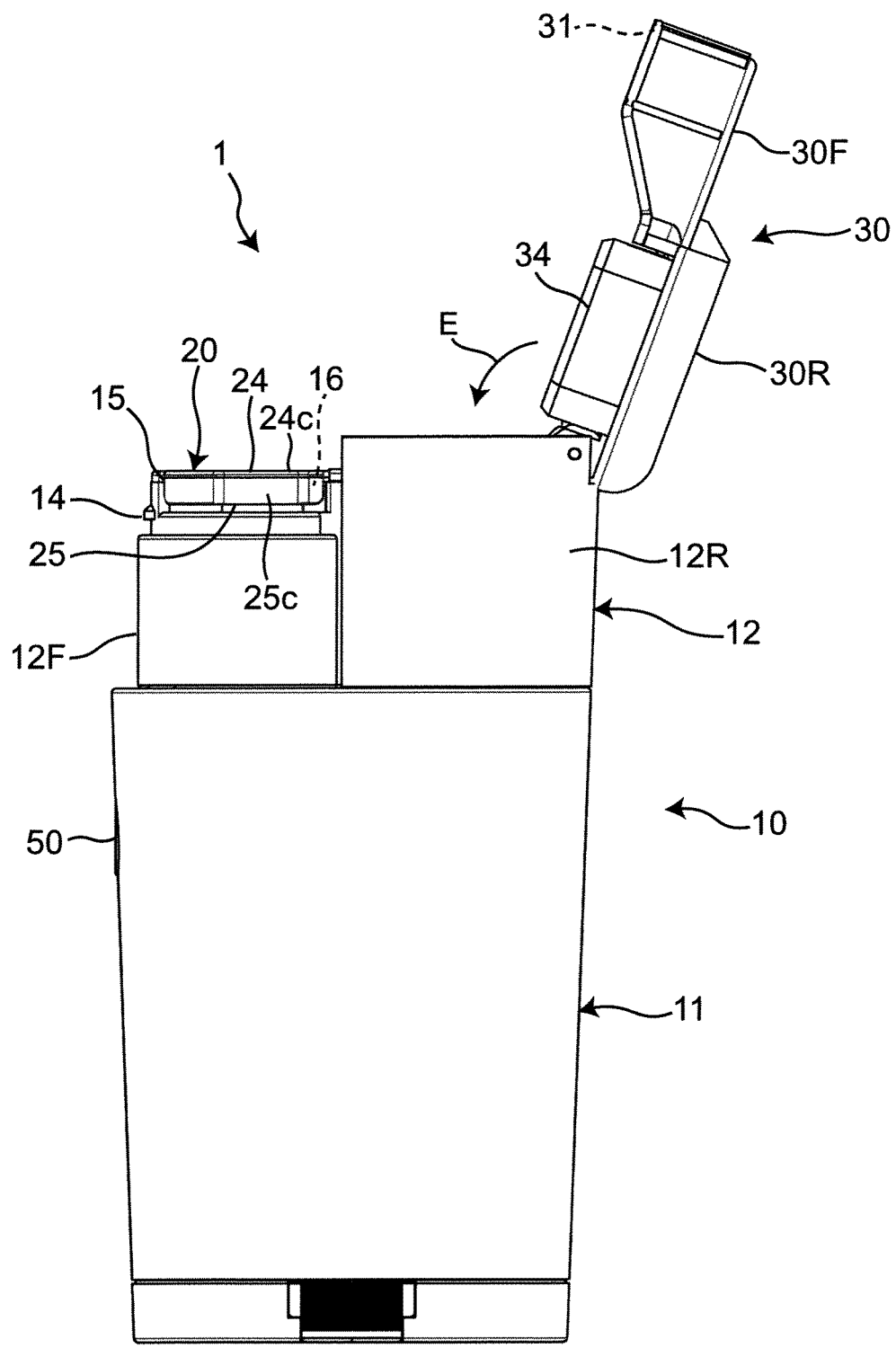
FIG. 4 is a view showing the mesh nebulizer in the mounted state in FIG. 3 as viewed from the right side.

As shown in FIGS. 3 and 4, the bottom plate portion 22 (supporting the sheet 21) of the replacement element 20 faces the bottom surface 16*b* of the recessed portion 16, and the sidewall portion 23 of the replacement element 20 faces the side surface 16*c* of the recessed portion 16. The flange portions 24*b* and 24*c* of the replacement element 20 overlap the left-side portion 15*b* and the right-side portion 15*c* of the edge portion 15 around the recessed portion 16 of the main body 10, respectively. Therefore, the user is able to easily mount the replacement element 20 in the recessed portion 16 of the main body 10 while the replacement element 20 is separated from the cap 30. This state is a mounted state.

Figure 6:
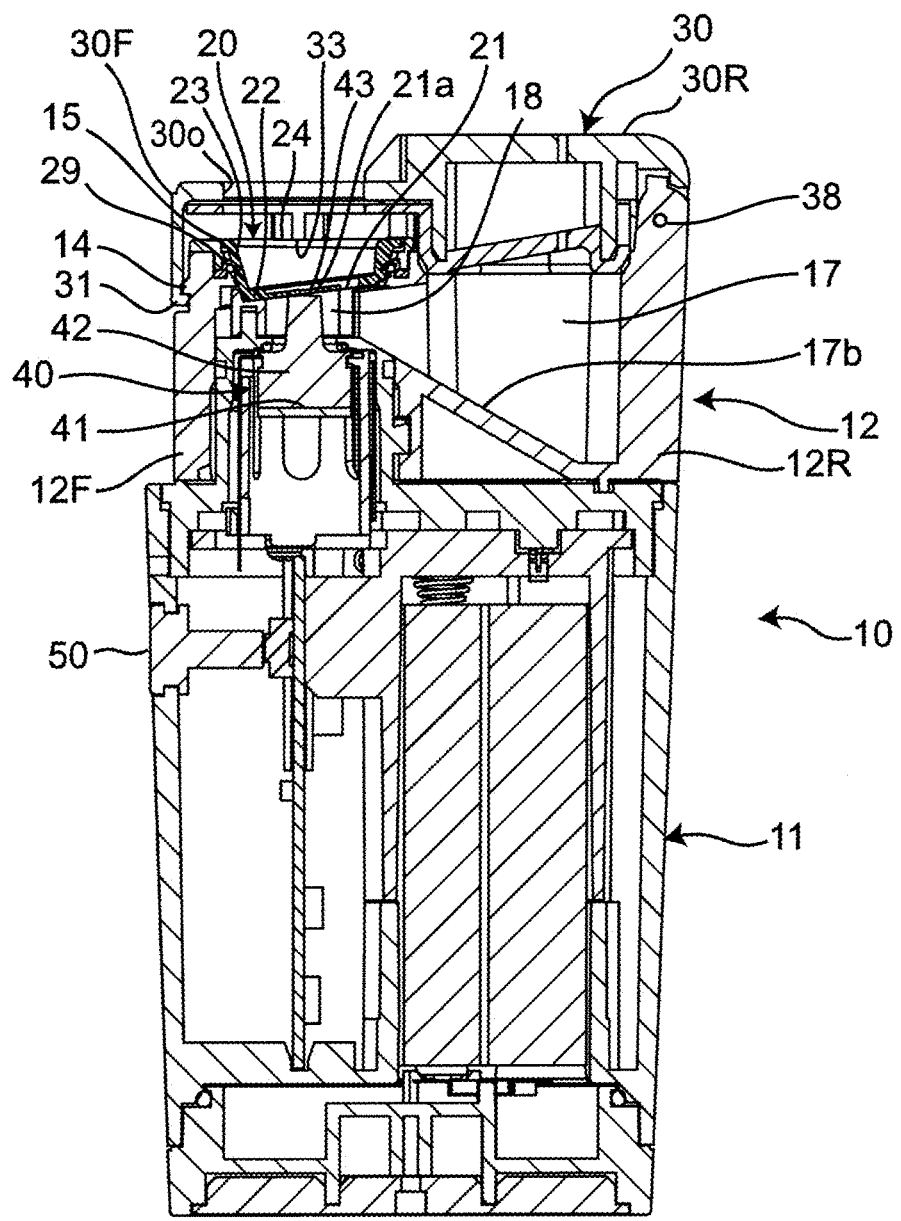
FIG. 6 is a view showing a longitudinal section when the mesh nebulizer in an assembled state is viewed from the right side.

In this mounted state, the user rotates and closes the cap 30 through the hinge 38 with respect to the main body 10 (the main body upper portion 12) as shown by an arrow E in FIG. 4. Then, the engagement protrusion 31 of the cap 30 vertically or substantially vertically engages with the engagement protrusion 14 of the main body upper portion 12. This fixes the cap 30 to the main body upper portion 12 in a closed state. Thus, as shown in FIG. 5A, the mesh nebulizer 1 is easily assembled. This state is an assembled state. FIGS. 5B and 5C are views showing the mesh nebulizer in FIG. 5A as viewed from the front and the top, respectively. FIG. 6 is a view showing a longitudinal section when the mesh nebulizer 1 in an assembled state is viewed from the right side.

In this assembled state, the mesa portion 34 of the cap 30 blocks the upper portion of the liquid storage portion 17 to significantly reduce or prevent overflow of a medicinal solution from the liquid storage portion 17. In addition, as shown in FIG. 7 (an enlarged view of the portion adjacent to or in a vicinity of the replacement element 20 in FIG. 6), in this assembled state, the protruding portions 33, 33 of the cap 30 protruding toward the main body upper portion 12 press the flange portions 24*b* and 24*c* (FIG. 7 shows only the flange portion 24*b*) together with the upper edge 23*a* of the sidewall portion 23 of the replacement element 20 toward the left-side portion 15*b* and the right-side portion 15*c* of the edge portion 15 around the recessed portion 16 of the main body 10. Therefore, the flange portions 24*b* and 24*c* are clamped between the protruding portions 33, 33 of the cap 30 and the left-side portion 15*b* and the right-side portion 15*c* of the edge portion 15 around the recessed portion 16 of the main body 10, and the replacement element 20 is firmly positioned with respect to the longitudinal axis direction of the main body 10. Accordingly, the mesh portion 21*a* of the replacement element 20 faces the vibration surface 43 of the vibrator 40 at a position corresponding to the bottom surface 16*b* of the recessed portion 16. Thus, the mesh nebulizer is easily assembled (this state is an assembled state).

In this assembled state, the mesh portion 21*a* faces the vibration surface 43 at an angle. Therefore, at the time of operation described below, a portion of the mesh portion 21*a* having an appropriate gap with respect to the vibration surface 43 sprays the medicinal solution.

As described above, the packing 29 is provided on the side surface 16*c* of the recessed portion 16 of the main body 10 and surrounds and be in contact with the sidewall portion 23 of the replacement element 20 in the circumferential direction. Accordingly, the packing 29 significantly reduces or prevents overflow of the medicinal solution supplied between the vibration surface 43 and the mesh portion 21*a*, at the time of operation as described herein, to the outside through the gap between the side surface 16*c* of the recessed portion 16 and the sidewall portion 23 of the replacement element 20.

Figure 10:
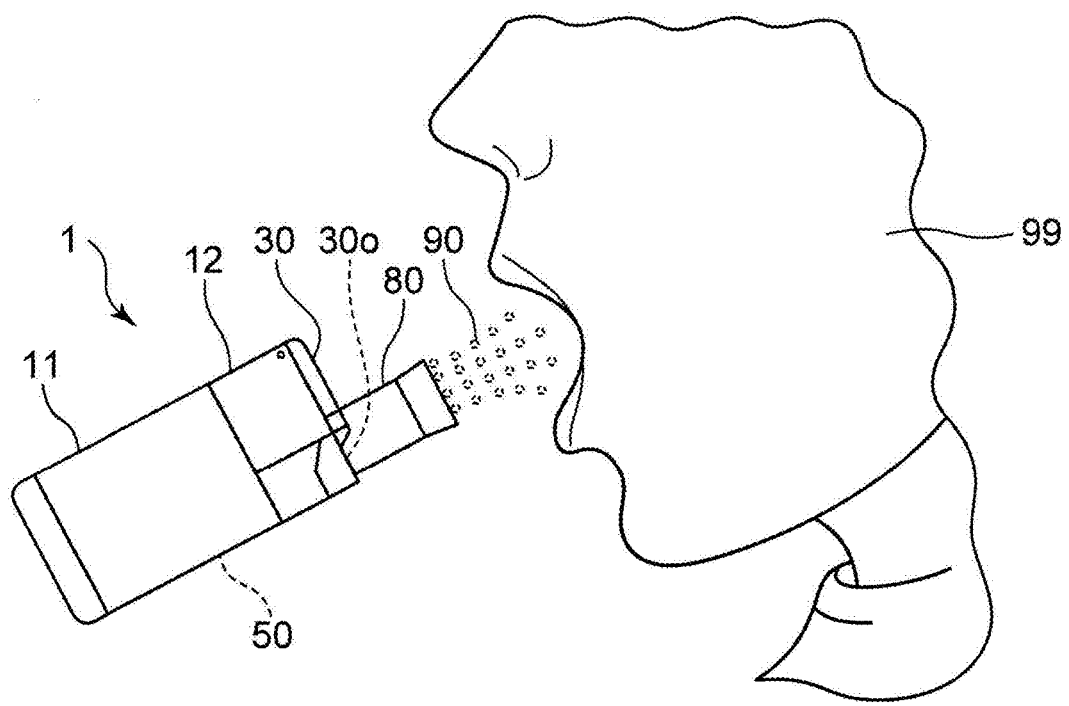
FIG. 10 is a view exemplifying a mode in which a user uses the mesh nebulizer.

Prior to operation of the mesh nebulizer 1, the user puts a medicinal solution in the liquid storage portion 17 of the main body upper portion 12. As shown in FIG. 10, the user detachably mounts, for example, a mouthpiece 80 to the opening 30*o* of the cap 30 in the assembled state. Note that, instead of the mouthpiece 80, an inhalation mask that covers the face of a user 99 may be mounted.

As shown in FIG. 10, when the user tilts the mesh nebulizer 1 slightly forward, the medicinal solution is supplied from the liquid storage portion 17 forming the liquid supplier onto the vibration surface 43 of the vibrator 40 through the liquid supply path 18. That is, the medicinal solution is supplied between the vibration surface 43 and the mesh portion 21a. When the user turns on the power switch 50, a drive voltage is applied to the ultrasonic transducer 41 of the vibrator 40, and the vibration surface 43 vibrates. Accordingly, the medicinal solution 90 is atomized and sprayed through the mesh portion 21a (more precisely, a plurality of through holes extending through the sheet 21).

After operation of the mesh nebulizer 1, the user removes the mouthpiece 80 and also removes the main body upper portion 12 from the main body lower portion 11. The cap 30 is opened with respect to the main body upper portion 12, and the replacement element 20 being separated from the cap 30 is removed from the recessed portion 16 of the main body 10. The user is able to easily hold the replacement element 20 by picking the knob margin portions 25b and 25c, together with the outer edges of the flange portions 24b and 24c of the replacement element 20, with the user's hand (for example, the thumb and the forefinger), from both sides (outside) toward the center. Therefore, the user is able to easily remove the replacement element 20 from the recessed portion 16 of the main body 10.

The user tilts the main body upper portion 12 and discharges the medicinal solution remaining in the liquid storage portion 17. Further, the mouthpiece 80 and the main body upper portion 12 are washed, disinfected, and dried. The main body lower portion 11 may be also cleaned, disinfected, and dried.

The replacement element 20 is typically discarded. In that case, the user does not need to clean, disinfect, and dry the replacement element 20 including the mesh portion 21a. Therefore, maintenance is simplified. Further, because the replacement element 20 is formed separately from the main body 10 and the cap 30 and includes a synthetic resin, the replacement element 20 is able to be manufactured relatively compactly and inexpensively. Therefore, a cost for the replacement element 20 is significantly reduced.

The planar shape of the recessed portion 16 of the main body upper portion 12 is circular or substantially circular. Accordingly, the planar shape of the bottom plate portion 22 and the sidewall portion 23 of the replacement element 20 is circular or substantially circular. However, the planar shape is not limited to this, and the planar shape of the recessed portion 16 may be another annular shape, for example, a round corner rectangle (a rectangular or substantially rectangular shape with rounded corners). The planar shape of the bottom plate portion and the sidewall portion of the replacement element 20 may be set according to the planar shape of the recessed portion 16.

As described above, a replacement element according to a preferred embodiment of the present invention is a replacement element of a mesh nebulizer that includes a main body and a cap that covers an upper portion of the main body. The main body of the mesh nebulizer includes a recessed portion that opens upward, a vibrator including a vibration surface at a position corresponding to a bottom surface of the recessed portion, and a liquid supplier to supply liquid toward the vibration surface of the vibrator. The replacement element includes a sheet including a mesh portion that faces the vibration surface, a bottom plate portion supporting a peripheral edge of the sheet, and a sidewall portion that is continuous with an outer edge of the bottom plate portion and faces a side surface of the recessed portion. The bottom plate portion includes a flat annular peripheral edge portion supporting an upper surface of the peripheral edge of the sheet and having an inner diameter larger than a diameter of the vibration surface, a flat ring portion that is concentric with the peripheral edge portion, has an outer diameter smaller than the inner diameter of the peripheral edge portion, and supports a corresponding portion of the sheet, and a plurality of elongated ribs radially connecting the peripheral edge portion and the ring portion to each other. The replacement element is separate from the main body and the cap, and is detachably mountable in the recessed portion of the main body while being separated from the cap prior to operation of the mesh nebulizer. When the replacement element is detachably mounted in the recessed portion of the main body while being separated from the cap prior to operation of the mesh nebulizer and the cap is closed with respect to the main body, the replacement element is positioned with respect to a longitudinal axis direction of the main body as the cap presses an upper edge of the sidewall portion toward an edge portion around the recessed portion of the main body.

The "mesh portion" refers to an element that has a plurality of through holes extending through a sheet and atomizes liquid by passing the solution through the through holes.

The planar shape of the recessed portion of the main body widely includes an annular shape, for example, a circular or substantially circular shape, a round corner rectangular shape (a rectangular or substantially rectangular shape with rounded corners) or the like. The planar shape of the sidewall portion of the replacement element is the same as or similar to the planar shape of the recessed portion.

The "longitudinal axis direction" of the main body generally refers to a vertical or substantially vertical direction.

The user who intends to operate the mesh nebulizer detachably mounts the replacement element in the recessed portion with a shape opening upward relative to the main body in a state where the cap opens with respect to the main body and the replacement element is separated from the cap. Accordingly, the bottom plate portion of the replacement element (supporting the peripheral edge of the sheet including the mesh portion) faces the bottom surface of the recessed portion, and also the sidewall portion of the replacement element faces the side surface of the recessed portion (this state is a mounted state). In this mounted state, the user closes the cap with respect to the main body. The cap then presses the upper edge of the sidewall portion of the replacement element toward an edge portion around the recessed portion of the main body, and positions the replacement element with respect to the longitudinal axis direction of the main body. Accordingly, the mesh portion of the replacement element faces the vibration surface of the vibrator at a position corresponding to the bottom surface of the recessed portion. Thus, the mesh nebulizer is easily assembled (this state is an assembled state).

When the mesh nebulizer is operated, the liquid supplier supplies liquid toward the vibration surface of the vibrator. With this operation, liquid is supplied between the vibration surface and the mesh portion. A drive voltage is then applied to the vibrator, and the vibration surface vibrates. Accordingly, the liquid is atomized and sprayed through the mesh portion (more precisely, a plurality of through holes extending through the sheet). Here, in the replacement element, the mesh portion of the sheet is maintained flatter by the ring portion. Therefore, the mesh portion is able to be to more accurately located with respect to the vibration surface in a state in which the replacement element is mounted in the recessed portion of the main body. Thus, the spray efficiency is able to be increased.

After operation of the mesh nebulizer, the user opens the cap with respect to the main body, and removes the replacement element being separated from the cap from the recessed portion. The replacement element is typically discarded. In that case, the user does not need to clean, disinfect, and dry the replacement element including the mesh portion. Therefore, maintenance is simplified. Further, because the replacement element is formed separately from the main body and the cap, the replacement element is able to be manufactured relatively compactly and inexpensively. Therefore, a cost for the replacement element is significantly reduced.

In the replacement element according to one preferred embodiment of the present invention, the sidewall portion gradually opens upward in correspondence with a side surface of the recessed portion of the main body.

In the replacement element according to this preferred embodiment, the sidewall portion gradually opens upward in correspondence with the side surface of the recessed portion of the main body. Accordingly, if the user places the replacement element around the recessed portion when mounting the replacement element, the sidewall portion of the replacement element is guided by the side surface of the recessed portion, and the bottom plate portion (which supports the peripheral edge of the sheet including the mesh portion) of the replacement element faces the bottom surface of the recessed portion. In addition, the sidewall portion of the replacement element faces the side surface of the recessed portion. Therefore, the user is able to easily mount the replacement element in the recessed portion of the main body.

The replacement element according to one preferred embodiment of the present invention further includes a flange portion continuous with and extending outward from the upper edge of the sidewall portion. When the cap is closed with respect to the main body in a mounted state where the replacement element is mounted in the recessed portion of the main body, the cap presses the flange portion together with the upper edge of the sidewall portion toward the edge portion around the recessed portion of the main body.

With respect to the flange portion, "outward" means that the flange portion is located outward when viewed from the center of the sidewall portion (or the bottom plate portion).

In the replacement element according to this preferred embodiment, when the cap is closed with respect to the main body in the mounted state, the cap presses the flange portion together with the upper edge of the sidewall portion toward the edge portion around the recessed portion of the main body. Therefore, the flange portion is clamped between the cap and the edge portion around the recessed portion of the main body, and the replacement element is firmly positioned with respect to the longitudinal axis direction of the main body.

In the replacement element according to one preferred embodiment of the present invention, a dimension of the flange portion that extends outward in an angular range around a center of the sidewall portion is larger than a dimension of the flange portion which extends outward in a remaining angular range other than the angular range.

In the replacement element according to this preferred embodiment, when mounting the replacement element in the recessed portion of the main body, the user is able to determine the azimuth around the center of the sidewall portion of the replacement element based on the dimension of the flange portion which extends outward.

In the replacement element according to one preferred embodiment of the present invention, the angular range is divided into two portions corresponding to azimuths opposite to each other around the center of the sidewall portion.

In the replacement element according to this preferred embodiment, the flange portion has two portions extending in the opposite azimuths. The user is able to easily hold the replacement element by picking the outer edges of the two portions of the flange portion with the user's hand (for example, the thumb and the forefinger), from both sides (outside) toward the center without touching the mesh portion with the user's fingers. Therefore, when mounting this replacement element, the user is able to easily mount the replacement element in the recessed portion of the main body. In particular, when the user mounts the replacement element while hand portions (for example, the little finger and the palm) other than those pinching the flange portions are in contact with a side surface of the main body or the like, it is possible to easily and significantly reduce or prevent the displacement (shake) of the hand with respect to the main body. Therefore, the user is able to further easily mount the replacement element in the recessed portion of the main body. After operation of the replacement element, the user is able to hold the replacement element by picking the outer edges of the portions of the flange portion which extend in the opposite azimuths with the user's hand (for example, the thumb and the forefinger) from both sides (outside) toward the center, to easily remove the replacement element from the recessed portion.

In the replacement element according to one preferred embodiment of the present invention, a planar shape of an outer edge of the flange portion is different from an original planar shape before rotation when rotated through about 180° around the center of the sidewall portion.

A "planar shape" of an outer edge of the flange portion refers to a shape in a plane perpendicular or substantially perpendicular to the center of the sidewall portion.

Assume that the planar shape of the outer edge of the flange portion has a two-fold rotational symmetry around the center of the sidewall portion. The user may attach (mistakenly) the replacement element to the main body in a posture rotated through about 180° around the center of the sidewall portion with respect to the proper posture. Thus, in the replacement element according to this preferred embodiment, a planar shape of an outer edge of the flange portion is different from an original planar shape before rotation when rotated through about 180° around the center of the sidewall portion. Accordingly, it is possible to prevent the replacement element from being attached (mistakenly) to the main body in a posture rotated through about 180° around the center of the sidewall portion with respect to the proper posture.

In the replacement element according to one preferred embodiment of the present invention, a planar shape of an outer edge of the remaining angular range of the flange portion fits on a ridge provided on the edge portion around the recessed portion of the main body.

In the replacement element according to this preferred embodiment, when mounting the replacement element, the user is able to position the replacement element with respect to the recessed portion in the circumferential direction by fitting a portion of the replacement element, which corresponds to the remaining angular range of the flange portion, on the ridge around the recessed portion of the main body.

The replacement element according to one preferred embodiment of the present invention further includes a knob margin portion that is continuous with and extends downward from an outer edge of the angular range of the flange portion.

In the replacement element according to this preferred embodiment, the user is able to more easily hold the replacement element by holding the knob margin portion together with the outer edge of the flange portion.

In the replacement element according to one preferred embodiment of the present invention, the bottom plate portion and the sidewall portion are homogeneously or substantially homogeneously and continuously integrated, and the sheet is bonded or welded to the bottom plate portion.

In the replacement element according to this preferred embodiment, the bottom plate portion and the sidewall portion are homogeneously or substantially homogeneously and continuously integrated, and the sheet is bonded or welded to the bottom plate portion. In other words, the replacement element is integrated including the sheet so that the user does not need to assemble and disassemble it. Accordingly, the mesh nebulizer is easily assembled. After operation of the mesh nebulizer, the replacement element is typically discarded, with the replacement element in one piece.

In the replacement element according to one preferred embodiment of the present invention, the sheet including the mesh portion is inclined with respect to a center of the sidewall portion and is inclined with respect to the vibration surface of the main body.

In an assembled state in which the replacement element according to this preferred embodiment is mounted in the recessed portion of the main body, the sheet including the mesh portion is inclined with respect to the vibration surface. Therefore, at the time of operation, the portion of the mesh portion having an appropriate gap with respect to the vibration surface sprays liquid.

In the replacement element according to one preferred embodiment of the present invention, each of the sheet, the bottom plate portion, and the sidewall portion includes a synthetic resin.

In the replacement element according to this preferred embodiment, each of the sheet, the bottom plate portion, and the sidewall portion includes a synthetic resin. Therefore, this replacement element is able to be manufactured at low cost.

Preferably, for example, each of the bottom plate portion, the sidewall portion, the flange portion, and the knob margin portion, which define the replacement element, includes a synthetic resin that is homogeneously or substantially homogeneously and continuously integrated. The bottom plate portion, the sidewall portion, the flange portion, and the knob margin portion is able to be manufactured at low cost by, for example, integral molding.

In another aspect, a mesh nebulizer according to a preferred embodiment of the present invention is a mesh nebulizer to atomize and spray liquid through a mesh portion. The mesh nebulizer includes a main body including a recessed portion that opens upward, the main body further including a vibrator including a vibration surface at a position corresponding to a bottom surface of the recessed portion, and a liquid supplier to supply liquid toward the vibration surface of the vibrator, a cap that covers an upper portion of the main body, and a replacement element separate from the main body and the cap and detachably mountable in the recessed portion of the main body while being separated from the cap prior to operation of the nebulizer. The replacement element includes a sheet including a mesh portion that faces the vibration surface, a bottom plate portion supporting a peripheral edge of the sheet, and a sidewall portion that is continuous with an outer edge of the bottom plate portion and faces a side surface of the recessed portion. The bottom plate portion includes a flat annular peripheral edge portion supporting an upper surface of the peripheral edge of the sheet and having an inner diameter larger than a diameter of the vibration surface, a flat ring portion that is concentric with the peripheral edge portion, has an outer diameter smaller than the inner diameter of the peripheral edge portion, and supports a corresponding portion of the sheet, and a plurality of elongated ribs radially connecting the peripheral edge portion and the ring portion to each other. When the replacement element is detachably mounted in the recessed portion of the main body while being separated from the cap prior to operation of the nebulizer and the cap is closed with respect to the main body, the replacement element is positioned with respect to a longitudinal axis direction of the main body as the cap presses an upper edge of the sidewall portion of the replacement element toward an edge portion around the recessed portion of the main body.

The user who intends to operate the mesh nebulizer detachably mounts the replacement element in the recessed portion with a shape opening upward relative to the main body in a state where the cap opens with respect to the main body and the replacement element is separated from the cap. Accordingly, the bottom plate portion of the replacement element (supporting the peripheral edge of the sheet including the mesh portion) faces the bottom surface of the recessed portion, and the sidewall portion of the replacement element faces the side surface of the recessed portion (this state is a mounted state). In this mounted state, the user closes the cap with respect to the main body. The cap then presses the upper edge of the sidewall portion of the replacement element toward an edge portion around the recessed portion of the main body, and positions the replacement element with respect to the longitudinal axis direction of the main body. Accordingly, the mesh portion of the replacement element faces the vibration surface of the vibrator at a position corresponding to the bottom surface of the recessed portion. Thus, the mesh nebulizer is easily assembled (this state is an assembled state).

When the mesh nebulizer is operated, the liquid supplier supplies liquid toward the vibration surface of the vibrator. With this operation, liquid is supplied between the vibration surface and the mesh portion. A drive voltage is then applied to the vibrator, and the vibration surface vibrates. Accordingly, the liquid is atomized and sprayed through the mesh portion (more precisely, a plurality of through holes extending through the sheet). Here, in the replacement element, the mesh portion of the sheet is maintained flatter by the ring portion. Therefore, the mesh portion is able to be to more accurately located with respect to the vibration surface in a state in which the replacement element is mounted in the recessed portion of the main body, and the spray efficiency is increased.

After operation of the mesh nebulizer, the user opens the cap with respect to the main body, and removes the replacement element being separated from the cap from the recessed portion. The replacement element is typically discarded. In that case, the user does not need to clean, disinfect, and dry the replacement element including the mesh portion. Therefore, maintenance is simplified. Further, because the replacement element is formed separately from the main body and the cap, the replacement element is able to be manufactured relatively compactly and inexpensively. Therefore, a cost for the replacement element is significantly reduced.

In the mesh nebulizer according to one preferred embodiment of the present invention, the side surface of the recessed portion of the main body gradually opens upward, and the sidewall portion of the replacement element gradually opens upward in correspondence with the side surface of the recessed portion of the main body.

In the mesh nebulizer according to this preferred embodiment, the side surface of the recessed portion of the main body gradually opens upward. The sidewall portion of the replacement element gradually opens upward in correspondence with the side surface of the recessed portion of the main body. Accordingly, if the user places the replacement element around the recessed portion when mounting the replacement element, the sidewall portion of the replacement element is guided by the side surface of the recessed portion, and the bottom plate portion (which supports the peripheral edge of the sheet including the mesh portion) of the replacement element faces the bottom surface of the recessed portion. In addition, the sidewall portion of the replacement element faces the side surface of the recessed portion. Therefore, the user is able to easily mount the replacement element in the recessed portion of the main body.

In the mesh nebulizer according to one preferred embodiment of the present invention, the replacement element includes a flange portion continuous with and extending outward from the upper edge of the sidewall portion, and, when the cap is closed with respect to the main body in a mounted state where the replacement element is mounted in the recessed portion of the main body, the cap presses the flange portion together with the upper edge of the sidewall portion of the replacement element toward the edge portion around the recessed portion of the main body.

In the mesh nebulizer according to this preferred embodiment, when the cap is closed with respect to the main body in the mounted state, the cap presses the flange portion together with the upper edge of the sidewall portion toward the edge portion around the recessed portion of the main body. Therefore, the flange portion is clamped between the cap and the edge portion around the recessed portion of the main body, and the replacement element is firmly positioned with respect to the longitudinal axis direction of the main body.

In the mesh nebulizer according to one preferred embodiment of the present invention, a dimension of the flange portion of the replacement element that extends outward in an angular range around a center of the sidewall portion is larger than a dimension of the flange portion which extends outward in a remaining angular range other than the angular range, a portion of the edge portion around the recessed portion of the main body, which corresponds to the remaining angular range of the flange portion, is provided with a ridge with a planar shape, and a planar shape of an outer edge of the remaining angular range of the flange portion is a shape fitted on the ridge provided on the edge portion around the recessed portion of the main body.

In the mesh nebulizer according to this preferred embodiment, the dimension of the flange portion of the replacement element which extends outward in the angular range around the center of the sidewall portion is larger than the dimension of the flange portion which extends outward in the remaining angular range other than the angular range. Accordingly, when mounting the replacement element in the recessed portion of the main body, the user is able to determine the azimuth around the center of the sidewall portion of the replacement element based on the dimension of the flange portion which extends outward. Further, according to the mesh nebulizer according to this preferred embodiment, a ridge having a planar shape is provided at a portion of the edge portion around the recessed portion of the main body, which corresponds to the remaining angular range of the flange portion. The planar shape of the outer edge of the remaining angular range of the flange portion of the replacement element fits on the ridge provided on the edge portion around the recessed portion of the main body. Accordingly, when mounting the replacement element, the user is able to position the replacement element in the recessed portion in the circumferential direction by fitting the portion of the flange portion of the replacement element, which corresponds to the remaining angular range, on the ridge around the recessed portion of the main body.

In the mesh nebulizer according to one preferred embodiment of the present invention, the vibration surface is perpendicular or substantially perpendicular to the longitudinal axis direction of the main body, and the mesh portion and the bottom plate portion of the replacement element are inclined with respect to a center of the sidewall portion and are inclined with respect to the vibration surface of the main body.

In the mesh nebulizer according to this preferred embodiment, the vibration surface is perpendicular or substantially perpendicular to the longitudinal axis direction of the main body. The mesh portion and the bottom plate portion of the replacement element are inclined with respect to the center of the sidewall portion and are inclined with respect to the vibration surface of the main body. Accordingly, in the assembled state, the sheet including the mesh portion is inclined with respect to the vibration surface. Therefore, at the time of operation, the portion of the mesh portion having an appropriate gap with respect to the vibration surface sprays liquid.

In the mesh nebulizer according to one preferred embodiment of the present invention, the side surface of the recessed portion of the main body is provided with a packing (e.g., an annular body) that surrounds and is contact with the sidewall portion of the replacement element in a circumferential direction.

In the mesh nebulizer according to this preferred embodiment, the packing significantly reduces or prevents overflow of the liquid supplied between the vibration surface and the mesh portion at the time of operation to the outside through the gap between the side surface of the recessed portion and the sidewall portion of the replacement element.

In the mesh nebulizer according to one preferred embodiment of the present invention, the cap is pivotally coupled to the main body by a hinge.

The mesh nebulizer according to this preferred embodiment allows the user to easily open and close the cap through the hinge with respect to the main body. Further, the cap will never be lost.

As is clear from the above, the replacement element and the mesh nebulizer according to the present invention allow the user to easily perform maintenance and significantly reduces a cost for the replacement element.

While preferred embodiments of the present invention have been described above, it is to be understood that variations and modifications will be apparent to those skilled in the art without departing from the scope and spirit of the present invention. The scope of the present invention, therefore, is to be determined solely by the following claims.

What is claimed is:

1. A replacement element for a mesh nebulizer including a main body and a cap to cover an upper portion of the main body, the main body including a recessed portion opening upward, a vibrator including a vibration surface at a position corresponding to a bottom surface of the recessed portion, and a liquid supplier to supply liquid toward the vibration surface of the vibrator, the replacement element comprising:

a sheet including a mesh portion that faces the vibration surface of the main body of the mesh nebulizer;

a bottom plate portion supporting a peripheral edge of the sheet; and a sidewall portion that is continuous with an outer edge of the bottom plate portion and faces a side surface of the recessed portion of the main body of the mesh nebulizer; wherein the bottom plate portion of the replacement element includes:

a flat annular peripheral edge portion supporting an upper surface of the peripheral edge of the sheet and having an inner diameter larger than a diameter of the vibration surface;

a flat ring portion that is concentric with the peripheral edge portion, has an outer diameter smaller than the inner diameter of the peripheral edge portion, and supports a corresponding portion of the sheet; and a plurality of elongated ribs radially connecting the peripheral edge portion and the ring portion to each other;

the replacement element is separate from the main body and the cap, and is detachably mountable in the recessed portion of the main body while being separated from the cap prior to operation of the mesh nebulizer;

when the replacement element is detachably mounted in the recessed portion of the main body while being separated from the cap prior to operation of the mesh nebulizer and the cap is closed with respect to the main body, the replacement element is positioned with respect to a longitudinal axis direction of the main body as the cap presses an upper edge of the sidewall portion toward an edge portion around the recessed portion of the main body.

2. The replacement element according to claim 1, wherein the sidewall portion opens upward in correspondence with a side surface of the recessed portion of the main body.

3. The replacement element according to claim 1, further comprising:

a flange portion that is continuous with and extends outward from the upper edge of the sidewall portion; wherein when the cap is closed with respect to the main body in a mounted state where the replacement element is mounted in the recessed portion of the main body, the cap presses the flange portion together with the upper edge of the sidewall portion toward the edge portion around the recessed portion of the main body.

4. The replacement element according to claim 3, wherein a dimension of the flange portion that extends outward in a predetermined angular range around a center of the sidewall portion is larger than a dimension of the flange portion which extends outward in a remaining angular range other than the predetermined angular range.

5. The replacement element according to claim 4, wherein the predetermined angular range is divided into two portions corresponding to azimuths opposite to each other around the center of the sidewall portion.

6. The replacement element according to claim 4, wherein a planar shape of an outer edge of the flange portion is different from an original planar shape before rotation when rotated through about 180° around the center of the sidewall portion.

7. The replacement element according to claim 4, wherein a planar shape of an outer edge of the remaining angular range of the flange portion fits on a ridge provided on the edge portion around the recessed portion of the main body.

8. The replacement element according to claim 4, further comprising a knob margin portion that is continuous with and extends downward from an outer edge of the predetermined angular range of the flange portion.

9. The replacement element according to claim 1, wherein the bottom plate portion and the sidewall portion are integral with each other; and the sheet is bonded or welded to the bottom plate portion.

10. The replacement element according to claim 1, wherein the sheet including the mesh portion is inclined with respect to a center of the sidewall portion and is inclined with respect to the vibration surface of the main body.

11. The replacement element according to claim 1, wherein each of the sheet, the bottom plate portion, and the sidewall portion includes a synthetic resin.

12. A mesh nebulizer for atomizing and spraying liquid through a mesh portion, the mesh nebulizer comprising:

a main body including a recessed portion opening upward, a vibrator including a vibration surface at a position corresponding to a bottom surface of the recessed portion, and a liquid supplier to supply liquid toward the vibration surface of the vibrator;

a cap that covers an upper portion of the main body; and a replacement element that is separate from the main body and the cap and is detachably mountable in the recessed portion of the main body while being separated from the cap prior to operation of the nebulizer; wherein the replacement element includes a sheet including a mesh portion that faces the vibration surface, a bottom plate portion supporting a peripheral edge of the sheet, and a sidewall portion that is continuous with an outer edge of the bottom plate portion and faces a side surface of the recessed portion;

the bottom plate portion includes:

a flat annular peripheral edge portion supporting an upper surface of the peripheral edge of the sheet and having an inner diameter larger than a diameter of the vibration surface;

a flat ring portion that is concentric with the peripheral edge portion, has an outer diameter smaller than the inner diameter of the peripheral edge portion, and supports a corresponding portion of the sheet; and a plurality of elongated ribs radially connecting the peripheral edge portion and the ring portion to each other; and when the replacement element is detachably mounted in the recessed portion of the main body while being separated from the cap prior to operation of the nebulizer and the cap is closed with respect to the main body, the replacement element is positioned with respect to a longitudinal axis direction of the main body as the cap presses an upper edge of the sidewall portion of the replacement element toward an edge portion around the recessed portion of the main body.

13. The mesh nebulizer according to claim 12, wherein the side surface of the recessed portion of the main body opens upward; and the sidewall portion of the replacement element opens upward in correspondence with the side surface of the recessed portion of the main body.

14. The mesh nebulizer according to claim 12, wherein the replacement element includes a flange portion that is continuous with and extends outward from the upper edge of the sidewall portion; and when the cap is closed with respect to the main body in a mounted state where the replacement element is mounted in the recessed portion of the main body, the cap presses the flange portion together with the upper edge of the sidewall portion of the replacement element toward the edge portion around the recessed portion of the main body.

15. The mesh nebulizer according to claim 14, wherein a dimension of the flange portion of the replacement element that extends outward in a predetermined angular range around a center of the sidewall portion is larger than a dimension of the flange portion which extends outward in a remaining angular range other than the predetermined angular range;

a portion of the edge portion around the recessed portion of the main body, which corresponds to the remaining angular range of the flange portion, is provided with a ridge; and a shape of an outer edge of the remaining angular range of the flange portion fits on the ridge provided on the edge portion around the recessed portion of the main body.

16. The mesh nebulizer according to claim 12, wherein the vibration surface is perpendicular or substantially perpendicular to the longitudinal axis direction of the main body; and the mesh portion and the bottom plate portion of the replacement element are inclined with respect to a center of the sidewall portion and are inclined with respect to the vibration surface of the main body.

17. The mesh nebulizer according to claim 12, wherein the side surface of the recessed portion of the main body is provided with an annular body that surrounds and is in contact with the sidewall portion of the replacement element in a circumferential direction.

18. The mesh nebulizer according to claim 12, wherein the cap is pivotally coupled to the main body by a hinge.

* * * * *